United States Patent [19]

Zivitz et al.

[11] Patent Number: 4,695,164
[45] Date of Patent: Sep. 22, 1987

[54] POSITION DETECTOR AND MOUNT THEREFOR FOR A CENTRIFUGAL ANALYZER

[75] Inventors: Maury Zivitz; Eric Ko; Mark Eslick, all of Houston, Tex.

[73] Assignee: Boehringer Mannheim GmbH, Mannaheim, Fed. Rep. of Germany

[21] Appl. No.: 779,520

[22] Filed: Sep. 24, 1985

[51] Int. Cl.[4] .................. G01N 21/90; G01N 1/10
[52] U.S. Cl. ................. 356/427; 250/231 SE; 356/246
[58] Field of Search ............ 250/231 SE, 237 G; 340/365 P; 356/246, 427; 436/45; 324/175

[56] References Cited

U.S. PATENT DOCUMENTS

| 2,685,083 | 7/1954  | Beman .        |           |
|-----------|---------|----------------|-----------|
| 2,948,890 | 8/1960  | Barth et al. . |           |
| 3,514,613 | 5/1970  | Mashburn       | 356/427 X |
| 3,555,284 | 1/1971  | Anderson       | 356/246 X |
| 3,576,441 | 4/1971  | Adams et al.   | 356/427 X |
| 3,712,742 | 1/1973  | Cohen          | 356/427 X |
| 3,756,402 | 9/1973  | Wagers, Jr. et al. | 356/427 X |
| 3,757,943 | 9/1973  | Chae et al.    | 356/427 X |
| 4,076,393 | 2/1978  | Bates .        |           |
| 4,157,802 | 6/1979  | May, Jr. .     |           |
| 4,506,339 | 3/1985  | Kühnlein       | 324/175 X |
| 4,515,889 | 5/1985  | Klose et al.   | 435/4     |
| 4,557,600 | 12/1985 | Klose et al.   | 356/246   |

FOREIGN PATENT DOCUMENTS

| 0141009 | 5/1985  | European Pat. Off. .    |
| 2450322 | 5/1976  | Fed. Rep. of Germany .  |
| 2852660 | 6/1980  | Fed. Rep. of Germany .  |
| 3314961 | 10/1984 | Fed. Rep. of Germany .  |

Primary Examiner—Eugene R. LaRoche
Assistant Examiner—Steven J. Mottola
Attorney, Agent, or Firm—Felfe & Lynch

[57] ABSTRACT

A relative position detector has a photodetector arrangement for providing light and responding to the intensity of the light when reflected thereto. A member such as a cylindrical pin having a surface reflective of the light, convex to the photodetector arrangement, and movable relative thereto reflectively sweeps the light across the photodetector arrangement for responding thereto to produce a continuously-curving response indicating with its peak the position detected. The continuously-curving response can be differentiated in a peak detector for even more precise position detection. A mount which may be used for the photodetector arrangement has a support member and a member having a lower coefficient of thermal expansion slidably supported thereon, except for one fixed point.

16 Claims, 3 Drawing Figures

POSITION DETECTOR AND MOUNT THEREFOR FOR A CENTRIFUGAL ANALYZER

The invention relates to a position detector for detecting a position of a member moving one portion of the position detector relatively across another portion of the position detector and a position detector for detecting a rotational position of a rotor of a centrifugal analyzer, more particularly, and to a mount therefor.

There are many examples of detecting a relative position of relatively-moving members. One example is detecting a rotational position of the rotor of a centrifugal analyzer to coordinate rotation of a cuvette on the rotor to an optical path for photometrically analyzing liquid in the cuvette with devices for the photometric analysis.

A centrifugal analyzer is described in U.S. Pat. No. 3,555,284 issued Jan. 12, 1971 to Anderson. It has a disk-shaped rotor having circumferentially-spaced, radial, liquid-flow passages. Rotation of the rotor centrifugally forces a liquid sample and reagent along each passage to a cuvette terminating each passage radially outwardly. Each cuvette has apertures providing an optical path through the cuvette along an axis parallel to the axis of rotor rotation. The cuvettes are concentric with the axis of rotor rotation so that rotation of the rotor also brings the optical path through each cuvette successively into alignment with a light source and photometric detector on opposite sides of the rotor. Detecting the intensity of the light from the optical path through each cuvette with the photometric detector then indicates the extent of any optical reaction of the reagent with the liquid sample to provide a quantitative analysis of the component of the liquid sample with which the reagent reacted.

In order to be able to relate each such centrifugal analysis to the liquid sample in each cuvette, however, a position detector must indicate the successive cuvettes rotated into the optical path from the light source through the cuvette to the photometric detector. The position detector of the centrifugal analyzer described in the above, Anderson patent is disclosed in U.S. Pat. No. 3,514,613 issued May 26, 1970.

Another position detector for indicating the alignment of the optical path through successive cuvettes with that of a light source and photometric detector in a centrifugal analyzer is disclosed in U.S. Pat. No. 3,576,441 issued Apr. 27, 1971 to Adams, et al. It uses circumferentially-spaced, radial slots through a disk rotated with the rotor having the cuvettes and a light source and photodetector on opposite ends of an optical path through the successive slots as the slotted disk is rotated.

Transmission (or interruption or knife-edge reflector) positional photodetectors of this type introduce considerable uncertainty, however, because the position-detecting waveform of the photodetector does not make a sharp enough distinction between detection and non-detection. Diffraction of the light as the slot (or interrupter) is rotated through the light and constant full (or null) intensity across the slot (or interrupter or knife-edge reflector) account for this, for example. Further, the detection is dependent on the actual speed of relative movement and the fineness of the light beam and detection feature (transmission slot, interrupter, or knife-edge reflector) which have practical limits.

As a result, threshold level devices were frequently included in such position-detecting circuitry as indicated in the above Adams et al. patent, for example, by a one-shot. Such threshold devices are, however, well known to introduce time and temperature variations which reduce the accuracy of the position detection sought to be improved thereby. In addition, in an arrangement like that shown in the above, Adams et al. patent in which the position-indicating slots are separate from the optical path through the rotor with the cuvettes, an additional, mechanical tolerance in aligning the slots and cuvettes is introduced.

These electrical and mechanical difficulties in detecting the positioning of each cuvette in the optical path between the light source and photometric detector for analyzing the contents of the cuvette become more acute in more modern and sophisticated centrifugal analyzers for several reasons. In order to minimize the volume of the liquid sample required for each analysis and to accommodate as many cuvettes around the rotor as possible, the cuvettes and thus the apertures therein defining the analysis light path should be made quite small. For example, apertures of 1.5 millimeter diameter in each cuvette would be desirable. The small apertures require more-precise position detection.

Further, rotation of the analyzer rotor at high speeds of about 700 rpm, for example, is desirable to hold the liquid to be analyzed centrifugally in the cuvette during the analysis against gravity and capillary forces, for example, which could draw the liquid out of the cuvette at lower speeds of rotation. High speed is also desirable to make successive analyses as quickly as possible which becomes particularly important when successive analyses at different wavelengths are to be conducted on each liquid sample. The high speed of rotation requires more-precise position detection.

Still further, features for flow-resistance mixing, features for successive addition of several reagents to the liquid sample, and features for stopping or slowing the centrifugal flow of the liquid sample to the cuvette to provide reaction or incubation time before the liquid reaches the cuvette for photometric analysis require a relatively-long flow path for the liquid sample to the cuvette. The cuvettes may be, therefore, about 140 millimeters from the axis of rotor rotation, for example. This long flow path to the cuvette compounds the precision problem from the high speed of rotor rotation.

With the small apertures of the optical path through each cuvette and the speed and radius of its rotation described, the apertures of each cuvette traverse the optical path for the analysis therethrough in about $10^{-5}$ second. This brief time emphasizes the need for precise detection of the rotational position of each cuvette as it passes through the optical path for photometric analysis of its contents in more modern and sophisticated centrifugal analyzers.

Modern requirements for precise position detection are, however, even more exacting because it is also desirable to use a flashlamp to illuminate the optical path for the photometric analysis. Flashlamp illumination is desirable to provide a sufficiently-broad spectrum to the light with sufficient intensity and, of course, to conserve energy and extend the life of the lamp in comparison to allowing it to remain on during the intervals in which no cuvette is aligned with the optical path for a photometric analysis. Precise position detection is also required in more modern and sophisticated centrifugal analyzers, therefore, to trigger the flashlamp in time for the photometric analysis.

A disposable test element having the liquid-flow passage and cuvette is also desirable in more modern and sophisticated centrifugal analyzers. One is described in U.S. Pat. No. 4,515,889 issued May 7, 1985 to Klose, et al. use of a disposable test element as disclosed in the Klose et al. patent introduces still another mechanical tolerance, however, in aligning the disposable test cartridge with the position detecting arrangement on the rotor of the analyzer. This makes eliminating the additional mechanical tolerance of a position-detecting arrangement which is separate from the analyzer rotor as disclosed in the above Adams et al. patent, for example, even more important.

The small size of the apertures of the cuvette desirable for more modern and sophisticated centrifugal analyzers also introduces alignment considerations radially from the axis of rotor rotation. The temperature of the liquid-flow passage and cuvette of such centrifugal analyzers may be controlled, but it is not feasible to control the temperature of other parts of the instrument, e.g. the photometric detector system and the structure mounting it, too. Temperature changes in the photometric system can, therefore, expand or contract the system sufficiently to shift the radial alignment of the optical path for the photometric analysis sufficiently to affect the analysis.

For example, considering that the distance from the rotational axis of a rotor of a more modern and sophisticated analyzer to the ring of cuvettes for the optical analyses may be about 15 cm for the reasons previously described and that a typical metal, like aluminum, for constructing the analyzer has a thermal expansion of $23.6 \times 10^{-6} K^{-1}$ and, furthermore, that ambient temperature changes of at least $dT = 12° K$ may be expected, the shift of the optical systems due to temperature variations reaches about 0.04 mm which is double the overall, acceptable tolerance of the optical system described above.

It might be proposed to overcome this problem, therefore, to use a material with a very low thermal expansion property to construct the analyzer. One such a material is, for example, a metal alloy sold for this property under the trademark INVAR. It and other low thermal expansion materials, however, are generally weak and/or brittle in strength and/or difficult to fabricate into the precise shape required.

Strength is required of materials for a more modern and sophisticated centrifugal analyzer, however, because its rotor has to be rotated very fast, up to 3500 rpm, for example, and in a program of variable speeds of rotation with very fast accelerations and decelerations for operating the mixing and flow-control features described above, for example. Further, this all has to be done without affecting the exact mounting of the photometric beam relative to the axis of rotor rotation and, therefore, requires fabrication into a precise shape. Furthermore, any vibrations to the main frame of the instrument should be suppressed as far as possible in order to avoid noise and other problems which can be caused by the vibrations like the malfunction of parts of the instrument or disturbance of the flow of the liquid in the disposables on the rotor, for example which requires both strength and precise-shape fabrication.

Another way of mounting the photometric analysis detector and positional photodetector to avoid thermal expansion or contraction problems would, therefore, be desirable.

SUMMARY OF THE INVENTION

It is, therefore, an object of the invention to provide a precision position detector and a mount therefor suitable for a centrifugal analyzer, in particular.

To this and other ends, the invention provides a position detector having a photodetector portion for providing light, a photodetector portion for responding to the intensity of the light when reflected thereto and a member having a surface reflective of the light, convex to the photodetector portions, and movable relative to the photodetector portions so as to sweep the light reflectively across the portion of the photodetector arrangement for responding thereto. At least most relative movements of the reflective, convex surface of the member transversely of the photodetector portions in a plane of the convexity will so sweep the reflected light.

The convexity of the reflective surface causes the light to sweep across the photodetector portion for responding thereto faster than the relative movement between the photodetector portions and the convex member. The convexity of the reflective surface is, therefore, selected such that the speed of the light sweep across the photodetector portion for responding thereto in relation to the width of the light beam provided the other photodetector portion produces a continuously-curving response to the intensity of the light reflectively swept thereacross.

The convexity of the reflective surface distinguishes the invention structurally from position detectors using a knife-edge reflector even if, technically, under magnification, for example, the knife-edge reflector could be considered curved because the word is used in its ordinary sense to mean a structure which appears convex to the eye. The same is true, vice versa, as the reflective surfaces which are only slightly curved, lie an imperfectly-flat or level-eyed mirror, for example.

The functions of the convex reflective surface of the invention in sweeping the reflected light and producing thereby a continuously-curving response confirm the structural distinction. A knife-edge or slightly-curved reflector does not teach that the reflected light should be sweepingly reflected, but rather that it should just be reflected momentarily from the knife edge or substantially planarly from the slightly-curved reflector. Similarly, the result sought from a knife edge or slightly-curved reflector is not a continuously-curving response, but rather one which is sufficiently discontinuous to detect the position with the discontinuity sufficiently precisely.

Because the convex reflective surface sweeps the reflected light across the photodetector arrangement for responding thereto faster than the relative motion therebetween, the continuously-curving response may be sufficiently precise for some applications of the position detector. In a preferred embodiment for a centrifugal analyzer, for example, in which very precise position detection is required, however, the continuously-curving response is first-order differentiated in a peak detector to determine the peak of the continuously-curving response from the zero-crossing of its slope. The concept of this preferred embodiment is, thereofre, that indirect, electronic peak detection of a continuously-curving position response is preferable to trying to generate a position-indicating, peaked function directly.

Another preferred embodiment has a temperature-insensitive mount which, in the preferred embodiment, is used for maintaining the radial position of the photodetector arrangement and a photometric analysis detector of a centrifugal analyzer. The mount is a compound structure in which a member of a material having a lower coefficient of thermal expansion is slidably supported on a member of another material, except at one, fixed, reference point. The material of lower coefficient of thermal expansion supports the structure to be mounted, the positional photodetector and photometric analysis detector in the preferred embodiment, at a distance from the reference point. The distance is, therefore, thermally responsive to the material of lower coefficient of thermal expansion because of the sliding support thereof while, at the same time, that material does not have to provide the structural strength or shape for the support which is, instead, provided by the other material.

Materials of low coefficient of thermal expansion are often expensive, insufficiently strong (brittle, for example), and difficult to fabricate into structural, support shapes. The compounds structure thus achieves their desired, low thermal expansion while avoiding their drawbacks.

DESCRIPTION OF THE DRAWINGS

A preferred embodiment which illustrates but does not limit the invention will now be described with reference to drawings in which.

DESCRIPTION OF THE PREFERRED EMBODIMENT

Figure 1:
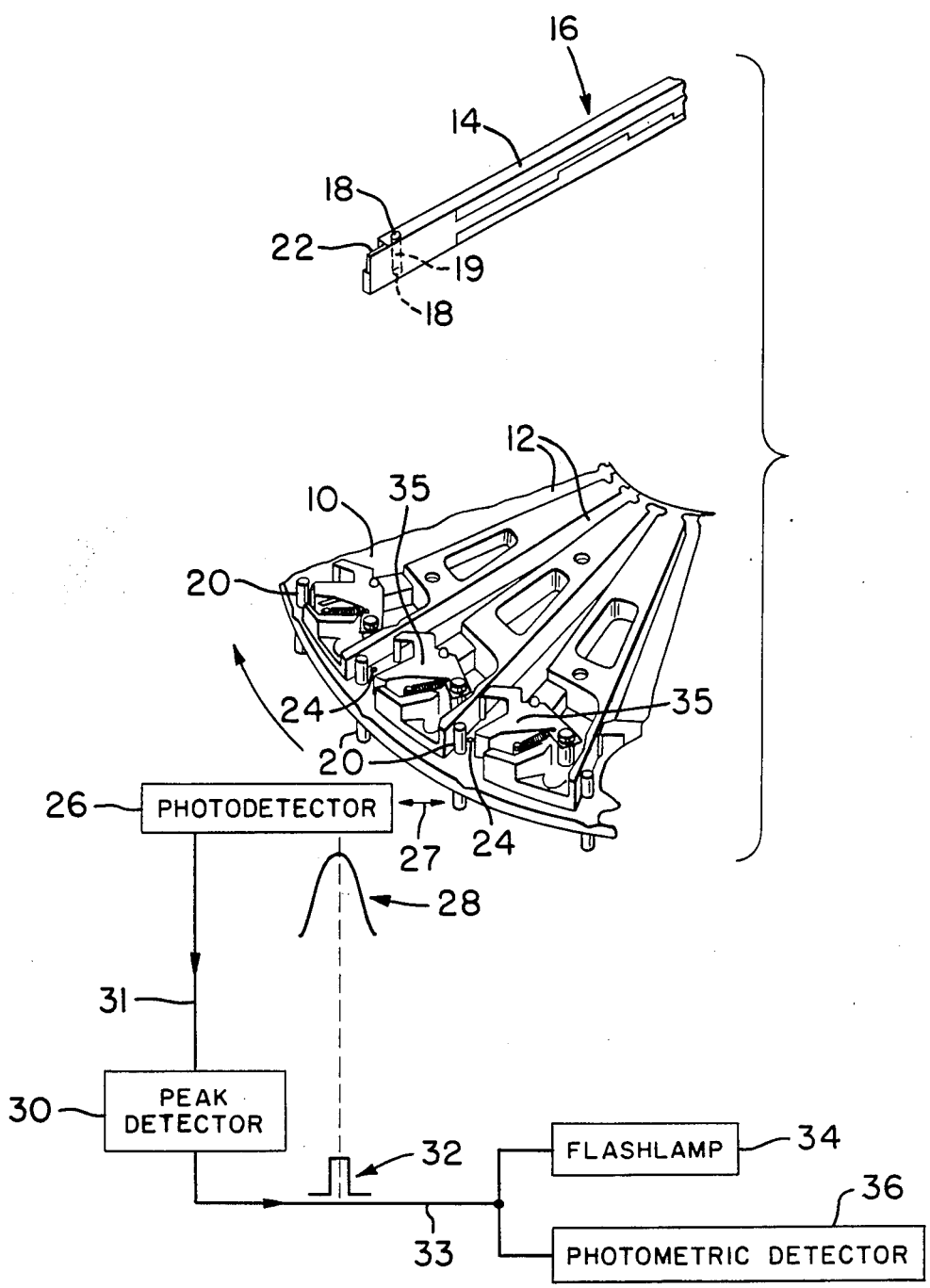
FIG. 1 is an, exploded perspective and schematic view of a portion of the preferred embodiment.

FIG. 1 shows a portion of a disk-shaped rotor 10 of a centrifugal analyzer. The rotor has circumferentially-spaced, radial channels 12 which are each configured to receive correspondingly a disposable test element 14 (only one shown). The disposable test element has an opening (not show) at the end at 16 which is radially innermost when the test element is received in one of the rotor channels 12 for receiving a liquid sample to be analyzed. Rotation of the rotor then centrifugally forces the liquid from the opening, along a passage (not shown) within the test element 14, and into a cuvette 19 which outwardly terminates the passage when the test element is in the rotor channel. The cuvette has a pair of apertures 18 which define an optical path through the cuvette for photometric analysis of the liquid, generally by its reaction with one or more reagents predisposed in the test element 14 and mixed with the liquid as it is centrifugally forced along the passage and into the cuvette where it is then held centrifugally. Further details of a preferred embodiment of the test element are described in the previously-referenced Klose et al. U.S. Pat. No. 4,515,889.

Figure 2:
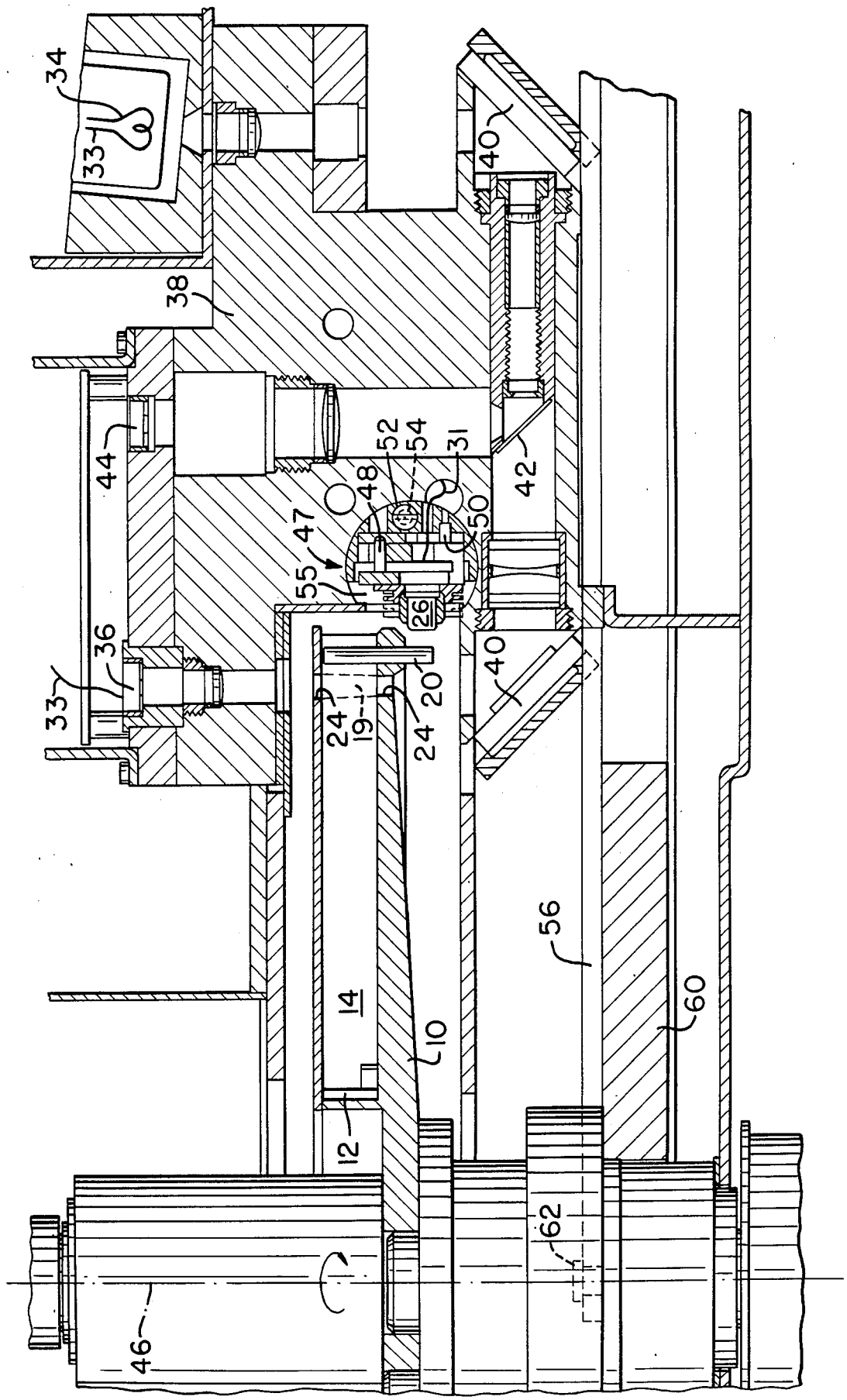
FIG. 2 is an elevation, partly in section, of a portion of the preferred embodiment shown in FIG. 1 and other portions thereof.

A cylindrical pin 20 is positioned in each channel 12 for cooperation with radial and circumferential locating surface of an L-shaped configuration 22 on the end of the test element with the cuvette. The pin 20 and configuration 22 cooperate to align the optical path through the cuvette defined by the apertures 18 with apertures 24 (both shown in FIG. 2) in each channel and to locate the test element and thus the optical path through the cuvette relative to the pin. The apertures 24 in the rotor could be enlarged to accommodate substantial positional inaccuracy but, as previously described, precise positional determination of the optical path through the cuvette in relation to photometric analysis devices triggered by the pin as described with reference to FIG. 2 is important.

For determining the rotational position of the optical path through the cuvette of the test element as it is rotated on the rotor relative to the optical path of the photometric devices (shown in FIG. 2) for analyzing the liquid in the cuvette, a portion of the same pin 20 which locates the test element and thus its optical path relative to the rotor cooperates with a photodetector 26. The photodetector has a portion which emits light which is reflected by the pin 20 as indicated by arrow 27 back to a portion of the photodetector for response thereto for detecting the position of the pin as it rotates past the photodetector. The convex surface of the cylindrical pin causes the light reflected to the photodetector to sweep across the photodetector response portion more rapidly than the rotation of the rotor but still produces a continuously-curving, intensity-dependent response from the photodetector as indicated at 28. Because of the more-rapid sweep of the reflected light, substantial accuracy in photodetector position detection of the pin can be achieved in this way alone.

Because the intensity-dependent response 28 of the photodetector 26 is continuously-curving, however, first-order differentiation in a peak detector 30 via line 31 produces an even more-precise positional indication on line 33 as indicated by the pulse at 32 where the differentiated continuously-curving function at 28 crosses zero (i.e. changes sign). Very precise position detection of the pin 20 relative to the photodetector 26 and, therefore, of the position of the optical path through the cuvette of the test element also determined by the pin, is achieved.

A clamp 35 in each channel 12 of the rotor 10 is arranged to use centrigugal and spring force to hold the radial and circumferential alignment surfaces of the L-shaped configuration 22 of the test element in each channel against the pin 20 to assure accurate positioning cooperation of the pin and configuration. Further details of the clamp 35 are disclosed in copending U.S. patent application Ser. No. 603,521, filed Apr. 24, 1984.

FIG. 2 shows more detail of the preferred embodiment of the photodetector 26 and its preferred use in a centrifugal analyzer. The photodetector is to detect rotation of each pin 20 (only one shown in FIG. 2) to a position in which the optical path through the cuvette 19 of a test element located on rotor 10 by cooperation with the pin aligns with an optical path in the centrifugal analyzer from a flashlamp 34 to a photometric detector 36 responsive to the intensity of the light traversing the optical path through the cuvette 19 and, thus, analyzing the liquid in the cuvette. The optical path from the flashlamp to the photometric detector extends through an optical unit 38 in which the position-detecting photodetector 26 is also mounted. Light from the flashlamp 34 is reflected by mirrors 40 through the optical path of the cuvette 19 and to the photometric detector 36. A beam splitter 42 in the optical path between the mirrors 40 directs another portion of the light from the flashlamp to another portion 44 of the photometric detector for reference. Various lenses and chromatic devices shown in the optical path from the flashlamp to the photometric detector and wavelength-defining filters (not shown) assure proper transmission of the light at wavelengths appropriate for analysis of the liquid in the cuvette.

The rotor 10 is mounted on bearings for rotation about an axis 46 as indicated by the arrow in FIG. 2. Each pin 20 is cylindrical with its axis parallel to the axis of rotation of the rotor. The relative position of a pin 20 and photodetector 26 when light emitted from the side of the photodetector toward the pin as shown in FIG. 2 can strike the pin for sweeping reflection across the same side of the photodetector as the rotor rotates the pin therepast is shown in FIG. 2.

As rotation of rotor 10 about its rotational axis 46 carries the pin 20 close enough towards the photodetector 26, light emitted by the photodetector generally toward the rotational axis 47 of the rotor strikes the pin and is reflected by the pin at a total reflected angle "g" given by the expression:

$$g = 2[Arctan\ (M) + Arctan\ (Y - Y_0/X - X_0)],$$

where:

g is the internal angle between the light incident on the pin and the light reflected by the pin;

M is the tangent of the angle of the incident light to the X axis of the cartesian coordinate system having an origin at the axis of rotor rotation;

$X_0$, $Y_0$ are the cartesian coordinates of the axis of the cylindrical pin; and X, Y are the cartesian coordinates of the point on the surface of the pin from which the light is reflected.

From this expression, it can be shown that the light emitted by the photodetector and reflected by the pin sweeps across an intensity-responsive portion the photodetector for detection more rapidly than the rotor rotation in dependence upon the radius of curvature of the pin. For example, when the axis of the pin is 140 millimeters from the rotational axis of the rotor and the pin has a radius of 2 millimeters and the rotor rotates at 750 rpm, the reflected light sweeps about 180° and thus across the photodetector with less than 1° of rotation of the rotor in about 0.18 milisecond. The width of the response function at 28 in FIG. 1 would, therefore, be even narrower in dependence upon the segment of the 180° light sweep to which the intensity-responsive portion of the photodetector 26 responds.

In some applications, the accuracy thus achieved by sweepingly reflecting light to a photodetector from a member convex to the photodetector, like pin 20, more rapidly than the relative movement therebetween may be sufficient. In the centrifugal analyzer of FIG. 2, however, the light path of cuvette 19 is about 1.5 mm in diameter and, at 750 rpm, therefore sweeps through the optical path to the photometric detector 36 in about $10^{-5}$ second. This leaves insufficient time for sufficient accuracy.

The light reflected from the pin could be made to sweep across the photodetector faster by making the radius of the pin smaller. This, however, is not a teaching of the invention for two reasons.

First, the pin 20 also serves to locate the test element 14 positionally to eliminate the tolerance of an additional member for this additional function. For this, in the preferred embodiment, pin 20 extends through the rotor 10 of the analyzer for locating the test element with the end of the pin projecting from one side of the rotor and reflecting light without the obstruction of the test element from an end of the pin projecting from the other side of the rotor. In order to achieve sufficient mechanical stability for the location function, the pin 20 should not be made too small.

Second, and more importantly, the invention recognizes the potential of differentiating the continuously-curving response function at 28. If the pin were made smaller to make the function 28 narrower, the time response of the photodetector and the other considerations described above would become significant enough to introduce error which can be avoided, instead, by differentiating the continuously-curving function in accordance with the preferred embodiment of the invention.

The photodetector 26 is preferably a commercial light emitting and sensing device such as a model HEDS-1000 made by Hewlett Packard. This model has a bifurcated aspheric lens (not shown, but on the left of photodetector 26 in FIG. 2) coincidingly focuses the light emitted and reflected light by the pin for sensing by corresponding photodiodes (not shown, but on the right of photodetector 26 in FIG. 2) for more-precise performance.

The photodetector is mounted in a cylindrical unit at 47 which is received in a cylindrical chamber in the optical unit 38. The cylindrical mounting unit at 47 for the photodetector has a positioning screw 48 for tilting the photodetector to aim it at the position of the pin 20 to be detected and a screw 50 for moving the photodetector toward and away from the axis 46 of rotor rotation to bring the focus of the emitted and reflected light onto the pin. These may be preset in relation to the optical properties of the photodetector and the surface of the cylindrical mounting unit which will support the photodetector in the optical unit. Each mounting unit 47 for a photodetector 26 will, however, still require some positional adjustment circumferentially of the rotor 10 to set the circumferential position of the photodetector appropriately in relation to the timing sequence of the flashlamp and the photometric detector (which may also be adjusted electronically in known ways not shown).

For this, a screw 52 is threaded into the mounting unit 47 and, with a portion 54 of the screw having a smaller diameter in the preferred embodiment shown, threaded into an end wall 55 of the optical unit 38. The portion of the screw 52 threaded into the mounting unit and the portion 54 threaded into the optical unit have different pitches. Rotation of screw 52 thus moves the mounting unit 47 in one direction and the screw in the opposite direction by differing amounts. The result of the opposite movements in different amounts is more-precise positioning relative to the rotation of the screw 52 and screw portion 54 than the threads of either would provide alone.

The photodetector 26 provides for circumferential position detection of the alignment of the optical path through the cuvette 19 of the test element 14 with that of the photometric detector 36 but does not provide for radial alignment relative to the axis 46 of rotation of the rotor 10. The radial alignment may vary, however, because of temperature differences between the rotor 10 and the optical unit 38. Such temperature differences are particularly apt to occur if the centrifugal analyzer has, as preferred, a device (not shown) for maintaining the space about the rotor 10 and thus the liquid to be analyzed in the cuvette of the test element thereon at a constant temperature different from ambient conditions and heat from the flash lamp 34 which affect the temperature of the optical unit 38.

Figure 3:
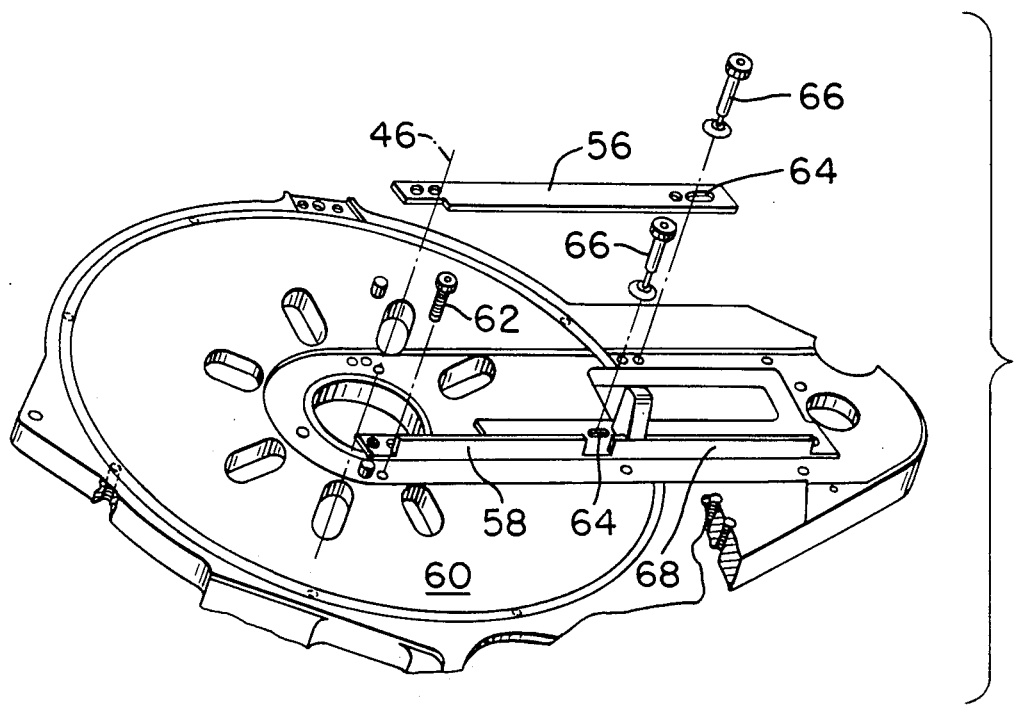
FIG. 3 is an exploded perspective view of a portion of the preferred embodiment shown in FIG. 2 and other portions thereof.

FIGS. 2 and 3 therefore show an arrangement for maintaining the radial alignment of the photometric detector 36 (FIG. 2) with the rotational axis 46 of the rotor 10 (FIG. 2) and, thus, with the optical path through the constant-temperature cuvette 19 (FIG. 2) of the test element. For this, parallel, generally-radial rails 56, 58 are secured at one end to a support plate 60 with fasteners 62 positioned at a reference point which, here, is on a normal between the rails diametrically across the axis 46 of rotor rotation. The rails 56, 58 are made from a material such as Invar having a lower coefficient of thermal expansion than the support plate. The other ends of the rails 56, 58 are secured to the plate 60 against displacement arcuately of the rotational axis 46 of the rotor but for movement transverse thereto with slots 64 and screw and spring washer fasteners 66. The optical unit 38 is then mounted on the rails 56, 58 at a distance from their fixed, reference point as shown in FIG. 2. As a result, the radial alignemnt of the optical unit 38 from the axis 46 of rotor rotation has the low coefficient of thermal expansion of the rails 56, 58 without regard to the expansion of the plate 60 which slides therebelow. The plate 60, however, provides the strength for supporting the rotor and optical unit. In addition, the material of the rails does not have to be made into the complex shape required for supporting the optical unit. The optical unit may, however, be given transverse, circumferential positional stability merely by a lip 68 along at least one of the rails, here rail 58.

It will be understood that the specification and examples are illustrative but not limitative of the present invention and that other embodiments within the spirit and scope of the invention will suggest themselves to those skilled in the art. As on specific examples it will be understood that other radiation could be substituted for the light of the described embodiments.

What is claimed is:

1. In a centrifugal analyzer having a support, a rotatable rotor on the support, and an optical unit radially spaced from the axis of rotor rotation and having an optical path for optically analyzing a liquid in a cuvette when on the rotor and rotated thereby to the optical path of the optical unit, a position detector for detecting the rotational position of the rotor relative to the optical unit in which the cuvette will be in the optical path of the optical unit for the optical analysis, comprising:
   a photodetector fixed to the support and having light emitting means for emitting light and light receiving means for responding to the intensity of the light when reflected thereto; and
   a member having a surface reflective of the light, convex to the photodetector, and movable with the rotor relative to the photodetector so as to sweep the light reflectively across the photodetector means for responding thereto for providing a continuously-curving response of the light receiving means.

2. The centrifugal analyzer of claim 1, wherein the member is a generally-cylindrical pin.

3. The centrifugal analyzer of claim 1, wherein the member comprises locating means for locating a test element on the rotor.

4. The centrifugal analyzer of claim 3, wherein the member comprises a generally-cylindrical pin extending through the rotor with the reflective surface on one side of the rotor and the locating means on the other side of the rotor.

5. The centrifugal analyzer of claim 1, and further comprising peak detector means for determining the zero crossing of the slope of the continuously-curving response of the photodetector means for responding to the light.

6. The centrifugal analyzer of claim 2, and further comprising peak detector means for determining the zero crossing of the slope of the continuously-curving response of the photodetector means for responding to the light.

7. The centrifugal analyzer of claim 3, and further comprising peak detector means for determining the zero crossing of the slope of the continuously-curving response of the photodetector means for responding to the light.

8. The centrifigal analyzer of claim 4, and further comprising peak detector means for determining the zero crossing of the slope of the continuously-curving response of the photodetector means for corresponding to the light.

9. The centrifugal analyzer of claim 1, and further comprising a mounting unit for the photodetector and a screw threaded into the mounting unit with threads of one pitch and sense and having a portion projecting therefrom for threading into a unit for supporting the mounting unit with threads of a different pitch and sense.

10. The centrifugal analyzer of claim 4, and further comprising a mounting unit for the photodetector and a screw threaded into the mounting unit with threads of one pitch and sense and having a portion projecting therefrom for threading into a unit for supporting the mounting unit with threads of a different pitch and sense.

11. The centrifugal analyzer of claim 5, and further comprising a mounting unit for the photodetector and a screw threaded into the mounting unit with threads of one pitch and sense and having a portion projecting therefrom for threading into a unit for supporting the mounting unit with threads of a different pitch and sense.

12. The centrifugal analyzer of claim 8, and further comprising a mounting unit for the photodetector and a screw threaded into the mounting unit with threads of one pitch and sense and having a portion projecting therefrom for threading into a unit for supporting the mounting unit with threads of a different pitch and sense.

13. The centrifugal analyzer of claim 1, wherein the pin extends through the rotor with its axis parallel to that of the rotor for reflecting the light from an end of the pin on one side of the rotor and locating the cuvette on the rotor with the end of the pin on the other side of the rotor.

14. The position detector of claim 1, and further comprising a pair of rails slidably supported on the support member, extending generally radially and parallel to each other from the axis of rotor rotation, and radially fixed to the support member only at points on a normal therebetween crossing the axis of rotor rotation for supporting the optical unit, the rails being made of a material having a lower coefficient of thermal epxansion than the support member.

15. A mount comprising:
   a support member of one material; and a slidable member of a material having a lower coefficient of thermal expansion than the material of the support member slidably supported on the support member, except at one point fixed to the support member, for receiving at a distance from the fixed point a unit to be supported thereby, the support member comprising a support for the rotor of a centrifugal analyzer and the slidable member extending generally radially from the axis of rotor rotation with the fixed point toward the axis of rotor rotation relative to the unit supported thereby, the unit being an optical unit of the centrifugal analyzer.

16. The mount of claim 15, wherein the slidable member comprises a rail having a lip extending generally radially therealong for providing transverse positional stability to the optical unit to be supported thereon.

* * * * *